(12) United States Patent
Dehghan Marvast et al.

(10) Patent No.: US 10,816,585 B2
(45) Date of Patent: Oct. 27, 2020

(54) TRACKING QUALITY CONTROL FOR ELECTROMAGNETIC GUIDANCE

(71) Applicant: KONINKLIJKE PHILIPS N.V., Eindhoven (NL)

(72) Inventors: Ehsan Dehghan Marvast, New York, NY (US); Shyam Bharat, Arlington, MA (US); Amir Mohammad Tahmasebi Maraghoosh, Melrose, MA (US); Sandeep M Dalal, Winchester, MA (US); Jochen Kruecker, Washington, DC (US); Cynthia Ming-Fu Kung, New York, NY (US); Niranjan Venugopal, Toronto (CA); Ananth Ravi, Toronto (CA)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 484 days.

(21) Appl. No.: 15/537,894

(22) PCT Filed: Dec. 9, 2015

(86) PCT No.: PCT/IB2015/059458
§ 371 (c)(1),
(2) Date: Jun. 20, 2017

(87) PCT Pub. No.: WO2016/103089
PCT Pub. Date: Jun. 30, 2016

(65) Prior Publication Data
US 2017/0363669 A1  Dec. 21, 2017

Related U.S. Application Data

(60) Provisional application No. 62/096,580, filed on Dec. 24, 2014.

(51) Int. Cl.
| | |
|---|---|
| *G01R 29/08* | (2006.01) |
| *A61N 5/10* | (2006.01) |
| *A61B 5/00* | (2006.01) |
| *A61B 5/06* | (2006.01) |

(Continued)

(52) U.S. Cl.
CPC .......... *G01R 29/0814* (2013.01); *A61B 5/062* (2013.01); *A61B 5/7221* (2013.01);
(Continued)

(58) Field of Classification Search
CPC ........ A61B 2017/00725; A61B 8/4245; A61B 8/4254; A61B 8/4263; A61B 5/061;
(Continued)

(56) References Cited

U.S. PATENT DOCUMENTS

| | | | | |
|---|---|---|---|---|
| 7,603,251 | B1 * | 10/2009 | Wiegert | G01V 3/081 |
| | | | | 702/152 |
| 8,326,402 | B2 * | 12/2012 | Govari | A61B 5/06 |
| | | | | 324/225 |

(Continued)

FOREIGN PATENT DOCUMENTS

JP   2000116790 A   4/2000

*Primary Examiner* — Son T Le
*Assistant Examiner* — Dustin R Dickinson

(57) ABSTRACT

An electromagnetic field quality assurance system employing an electromagnetic field generator (10) for emitting an electromagnetic field (12), and one or more quality assurance electromagnetic sensors (11, 21, 31, 41, 50) for sensing the emission of the electromagnetic field (12). The system further employs a quality assurance controller (74) for assessing a tracking quality of the electromagnetic field (12) derived from a monitoring of a sensed position of each quality assurance electromagnetic sensor (11, 21, 31, 41, 50) within a field-of-view of the electromagnetic field (12). The electromagnetic field generator (10), an ultrasound probe (20), an ultrasound stepper (30) and/or a patient table (40) may be equipped with the quality assurance electromagnetic sensor(s) (11, 21, 31, 41, 50).

16 Claims, 3 Drawing Sheets

(51) Int. Cl.
*A61B 34/20* (2016.01)
*A61B 10/02* (2006.01)
*A61B 17/00* (2006.01)

(52) U.S. Cl.
CPC ............ *A61B 34/20* (2016.02); *A61N 5/1001* (2013.01); *A61N 5/1075* (2013.01); *A61B 10/02* (2013.01); *A61B 2017/00725* (2013.01); *A61B 2034/2051* (2016.02); *A61N 2005/1051* (2013.01)

(58) Field of Classification Search
CPC ....... A61B 5/062; A61B 5/7721; A61B 10/02; A61B 34/20; A61B 2034/2051; G01R 29/0814; A61N 5/1001; A61N 5/1075; A61N 2005/1051; G01B 7/003; G01B 7/004; G01B 7/008
See application file for complete search history.

(56) References Cited

U.S. PATENT DOCUMENTS

| | | | |
|---|---|---|---|
| 9,522,045 | B2 | 12/2016 | Ramachandran et al. |
| 2005/0107687 | A1 | 5/2005 | Anderson |
| 2006/0122497 | A1* | 6/2006 | Glossop ................. A61B 34/20 600/424 |
| 2010/0156399 | A1* | 6/2010 | Chiba ................ A61B 5/14539 324/207.13 |
| 2010/0168556 | A1 | 7/2010 | Shen et al. |
| 2013/0102891 | A1* | 4/2013 | Binnekamp .......... A61N 5/1007 600/424 |
| 2014/0243671 | A1* | 8/2014 | Holl ..................... A61B 8/4209 600/443 |
| 2015/0051861 | A1 | 2/2015 | Kruecker et al. |
| 2017/0014192 | A1 | 1/2017 | Bharat et al. |

* cited by examiner

TRACKING QUALITY CONTROL FOR ELECTROMAGNETIC GUIDANCE

CROSS-REFERENCE TO PRIOR APPLICATIONS

This application is the U.S. National Phase application under 35 U.S.C. § 371 of International Application Serial No. PCT/IB2015/059458, filed on Dec. 9, 2015, which claims the benefit of U.S. Application Ser. No. 62/096,580, filed on Dec. 24, 2014. These applications are hereby incorporated by reference herein.

The present invention generally relates to tracking quality of electromagnetic field ("EMF") emitted for electromagnetic guidance during an interventional procedure (e.g., a transrectal biopsy, a transperineal biopsy, a low dose rate brachytherapy and a high dose rate brachytherapy). The present invention specifically relates to assessing inhomogeneity degree of electromagnetic field ("EMF") based on a monitoring of quality assurance electromagnetic sensor(s) within a field-of-view of the EMF (i.e., calibrated tracking area of the EMF).

In brachytherapy procedures involving electromagnetic guidance, an electromagnetic field generated by an EMF generator is located close to an anatomical region of interest. A typical EMF generator has a limited field of view ("FOV") (e.g., a 50×50×50 cm FOV for a typical brick EMF generator). A tracking accuracy of the EMF generator depends on a relative distance and position of each tracked device with respect to the EMF generator and also depends on a presence of any metallic object(s) in the FOV. Generally, the EMF generator and the tracked device(s) cannot be placed in a constant configuration for every interventional procedure in view of variations among the interventional procedures in terms of a geometry of the patients, the operating environment and a preference of a work flow by different physicians.

In case of prostate brachytherapy, the EMF generator may be placed above, beside or below the patient with variable distances from the tracked device(s). The tracked devices are generally, a six (6) degree-of-freedom ("DoF") reference sensor attached to the brachytherapy stepper, a six (6) DoF sensor attached to a transrectal ultrasound ("TRUS") probe, and a five (5) DoF sensor inside a tracked needle or guidewire. Due to the inhomogeneity of the electromagnetic field from temporal noise, the tracking accuracy and precision is variable, even inside the FOV of an undistorted electromagnetic field.

As a position of the EMF generator with respect to the tracked device(s) in an operating room is variable, it is imperative to have a quality control to show whether the tracking data is reliable. In addition, metallic object(s) may be introduced into the FOV of the EMF during the operation that may cause distortion in the EMF and reduction of tracking accuracy. The present invention provides methods, systems and devices for tracking quality control of the EM-tracking data. By monitoring the signal from the quality control system, an operator of the EM guidance may be informed whether the operator may trust the EM tracking information (e.g., a green image/icon on a graphical user interface ("GUI") signals reliable tracking information and a red image/icon on a GUI signals unreliable tracking information). The quality assurance data from the system/device may also assist the operator in initial placement of the EMF generator so that high quality measurements are obtained.

One form of the present invention is an electromagnetic field quality assurance system employing an electromagnetic field generator for emitting an electromagnetic field, and one or more quality assurance electromagnetic sensors for sensing the emission of the electromagnetic field. The system further employs a quality assurance controller for assessing a tracking quality of the electromagnetic field derived from a monitoring of a sensed position of any quality assurance electromagnetic sensor within the electromagnetic field. The electromagnetic field generator, an ultrasound probe, an ultrasound stepper and/or a patient table may be equipped with the quality assurance electromagnetic sensor(s).

For purposes of the present invention, the term "electromagnetic sensor" broadly encompasses all sensors capable of being induced by an electromagnetic field to generate a signal (e.g., a voltage) detectable for purposes of sensing a position and/or an orientation of the sensor and any associated object(s) (e the EMF generator, the ultrasound probe, the ultrasound stepper and/or the patient table) relative to a reference. An example of an electromagnetic sensor includes, but is not limited to, a sensor coil commercially available as a component of the Aurora® Electromagnetic Tracking System.

For purposes of the present invention, the term "quality assurance" as a modifier of the term "electromagnetic sensor" is used strictly for denoting a specific purpose of assessing a tracking quality of an electromagnetic field distinguishable from a purpose of tracking an ultrasound probe and additional interventional tools relative to a reference electromagnetic sensor.

For purposes of the present invention, the term "EMF generator" broadly encompasses all EMF generators having a structural configuration known in the art prior to and subsequent to the present invention for controlling an emission of an electromagnetic field, particularly for tracking interventional tool(s) (e.g., ultrasound probe, catheter, needle, etc.) via electromagnetic sensors during an interventional procedure (e.g., transrectal and transperineal biopsies and low dose rate and high dose rate brachytherapies). An example of an EMF generator includes, but is not limited to, an EMF generator commercially available as a component of the Aurora® Electromagnetic Tracking System.

For purposes of the present invention, the term "tracking quality" broadly encompasses a degree of inhomogeneity and/or distortion of the electromagnetic field emitted by an EMF generator that facilitates or inhibits an accurate sensing of a position and/or orientation of an electromagnetic sensor and any associated object(s).

For purposes of the present invention, the term "ultrasound probe" broadly encompasses any ultrasound probe as known in the art employing one or more ultrasound transducers/transmitters/receivers for projecting an ultrasound plane intersecting an anatomical region. Examples of an ultrasound probe include, but are not limited to, two-dimensional and three-dimensional ultrasound probes with sector, curvilinear or linear geometries.

For purposes of the present invention, the term "ultrasound stepper" broadly encompasses all steppers having a structural configuration known in the art prior to and subsequent to the present invention for facilitating a linear positioning and/or an angular positioning of an ultrasound probe during an interventional procedure. An example of an ultrasound stepper includes, but is not limited to, an ultrasound stepper commercially available as the Multi-Purpose Workstation™ Stepper.

For purposes of the present invention, the term "quality assurance controller" broadly encompasses all structural configurations of an application specific main board or an application specific integrated circuit housed within or linked to a computer or another instruction execution device/system for controlling an application of various inventive principles of the present invention as subsequently described herein. The structural configuration of the quality assurance controller may include, but is not limited to, processor(s), computer-usable/computer readable storage medium(s), an operating system, peripheral device controller(s), slot(s) and port(s). Examples of a computer includes, but is not limited to, a server computer, a client computer, a workstation and a tablet.

A second form of the present invention is the quality assurance controller employing an electromagnetic sensor monitoring module for monitoring a sensed position of each quality assurance electromagnetic sensor within a field-of-view of the electromagnetic field, and a quality assessment module assessing the tracking quality of the electromagnetic field derived from a monitoring of the sensed position of any quality assurance electromagnetic sensor within the field-of-view of the electromagnetic field.

For purposes of the present invention, the term "module" broadly encompasses an application component of the quality assurance controller consisting of an electronic circuit or an executable program (e.g., executable software and/firmware).

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

To facilitate an understanding of the present invention, exemplary embodiments of the present invention will be provided herein directed an example of quality assurance assessment of a tracking quality of an EMF field during a brachytherapy procedure. Nonetheless, those having ordinary skill in the art will understand how to make and use the present invention for various interventional procedures involving deviations of or alternatives to the clinical set-up shown in FIGS. 1 and 2.

For purposes of the present invention, the terms of the art including, but not limited to "field-of-view", "intervention", "calibration", "quality assurance", "tracking", "temporal" and "registration", are to be interpreted as known in the art of the present invention and exemplary described herein.

Figure 1:
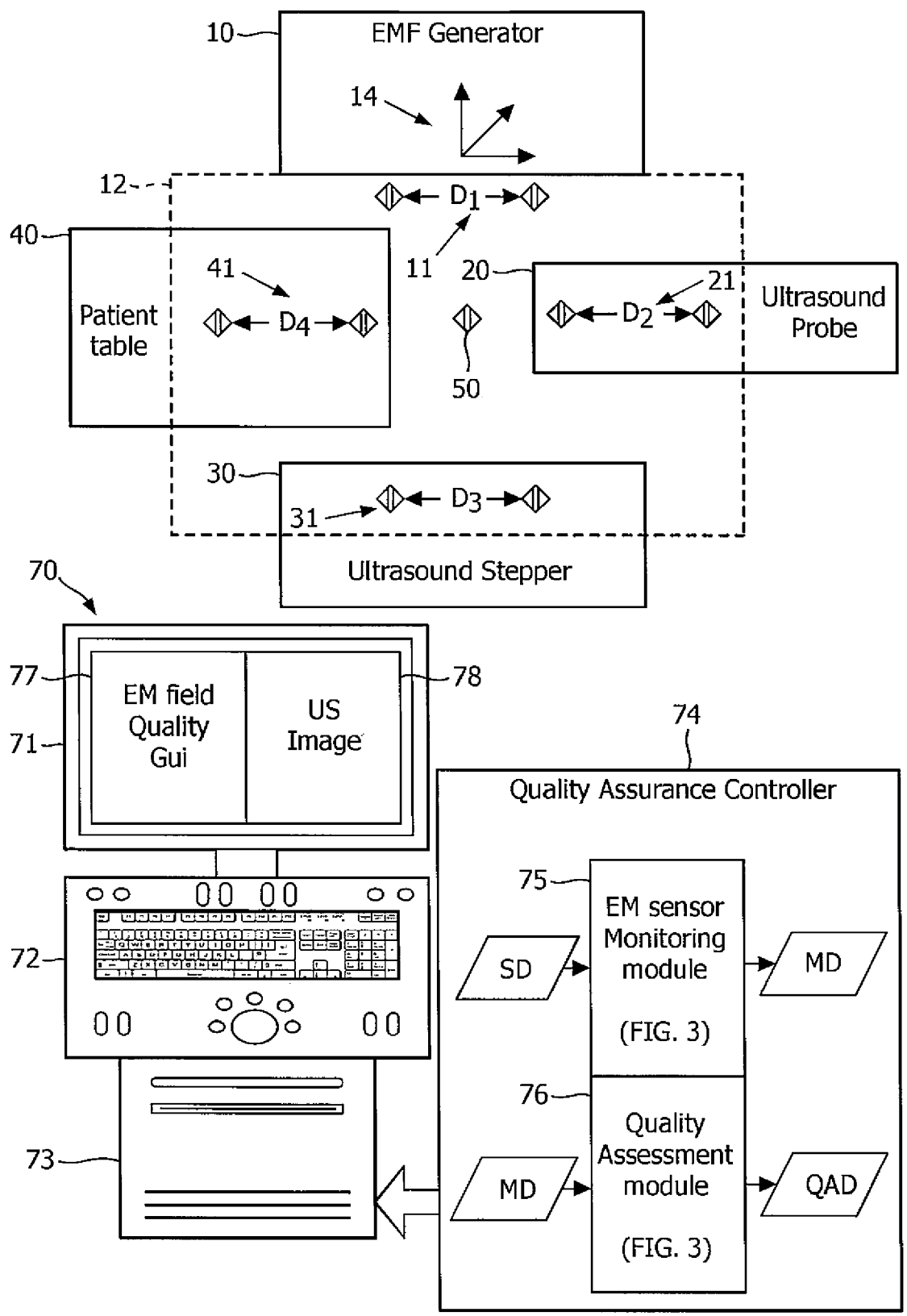
FIG. 1 illustrates an exemplary embodiment of an EMF quality assurance system in accordance with the present invention.

Referring to FIG. 1, a clinical set-up for a typical brachytherapy procedure involves a known clinical set-up of an EMF generator 10, an ultrasound stepper 30 and a patient table 40 whereby an ultrasound probe 20 may be translated and/or rotated by ultrasound stepper 30 as needed to generate ultrasound images of a patient (not shown) resting on patient table 40, and whereby EMF generator 10 emits an EMF field for tracking the translation and/or rotation of ultrasound probe 20 and additional interventional tool(s) (e.g., a needle, a catheter, etc.) within a field-of-view ("FOV") 12 of the EMF field relative to a reference electromagnetic sensor 50.

A EMF quality assurance ("QA") assessment of the present invention incorporates, into the clinical set-up, one or more QA electromagnetic sensors provided by EMF generator 10, ultrasound probe 20, ultrasound stepper 30 and/or patient table 40. In practice, each QA electromagnetic sensor may have any degrees of freedom deemed suitable for QA purposes (e.g., five (5) degrees or six (6) degrees).

Specifically, in practice, reference electromagnetic sensor 50 has a fixed position within the clinical set-up that positions reference electromagnetic sensor 50 within an emission of EMF field 12 to thereby serve as a reference for the tracking of ultrasound probe 20 and additional interventional tool(s). For example, referring to FIG. 2, reference electromagnetic sensor 50 may be removably mounted or affixed to a grid 60 as known in the art for guiding a needle and/or a catheter within a patient (not shown). In this position, reference electromagnetic sensor 50 serves as a tracking reference as known in the art and may further serve a QA electromagnetic sensor as subsequently described herein.

Referring back to FIG. 1, in practice, EMF generator 10 may be equipped with one or more QA electromagnetic sensors in any manner that positions the QA electromagnetic sensor(s) within a field-of-view 12 of the EMF. For example, referring to FIGS. 1 and 2, EMF generator 10 is equipped with a QA electromagnetic sensor pair 11 having a known physical distance $D_1$ between sensor pair 11 via a plastic (or other non-metallic material) attachment 13 is structurally configured to establish and maintain the known physical distance $D_1$ between a right sensor 11R and a left sensor 11L achieved through a precise design/manufacturing, independent measurements and/or EM measurements in a clean environment. Attachment 13 is removably mounted or affixed to EMF generator 10 whereby sensors 11R and 11L are positioned within FOV 12 of the EMF as shown.

Referring back to FIG. 1, in practice, ultrasound probe 20 may be equipped with one or more QA electromagnetic sensors in any manner that positions the QA electromagnetic sensor(s) within FOV 12 of the EMF. For example, referring to FIGS. 1 and 2, ultrasound probe 20 may be equipped with a QA electromagnetic sensor pair 21 having a known physical distance $D_2$ via an EM-compatible sleeve covering ultrasound probe 20 having a front sensor 21F and rear sensor 21R arranged thereon at known physical distance $D_2$ achieved through a precise design/manufacturing, independent measurements and/or EM measurements in a clean environment.

Referring back to FIG. 1, in practice, ultrasound stepper 30 may be equipped with one or more QA electromagnetic sensors in any manner that positions the QA electromagnetic sensor(s) within FOV 12 of the EMF. For example, referring to FIGS. 1 and 2, ultrasound stepper 30 may be equipped with a QA electromagnetic sensor pair 31 along translation rails 32 having known physical distance $D_3$ achieved through a precise design/manufacturing, independent measurements and/or EM measurements in a clean environment. Additionally, an encoder 61 (e.g., a linear encoder or a rotary encoder as known in the art) may be coupled to or integrated with ultrasound stepper 30 to measure a translation or a rotation (i.e., a motion) of ultrasound probe 20 with respect to some stationary location on the stepper. This measure can be calibrated (in a clean environment) to the EM reading of a sensor on the probe (w.r.t. a stationary sensor on the stepper) and used for QA subsequently.

Referring back to FIG. 1, in practice, patient table 40 may be equipped with one or more QA electromagnetic sensors in any manner that positions the QA electromagnetic sensor(s) within FOV 12 of the EMF. For example, referring to FIGS. 1 and 2, a portion of patient table 40 adjacent ultrasound stepper 30 may be equipped with a QA electromagnetic sensor pair 41 having known physical distance $D_4$ achieved through a precise design/manufacturing, independent measurements and/or EM measurements in a clean environment.

Figure 2:
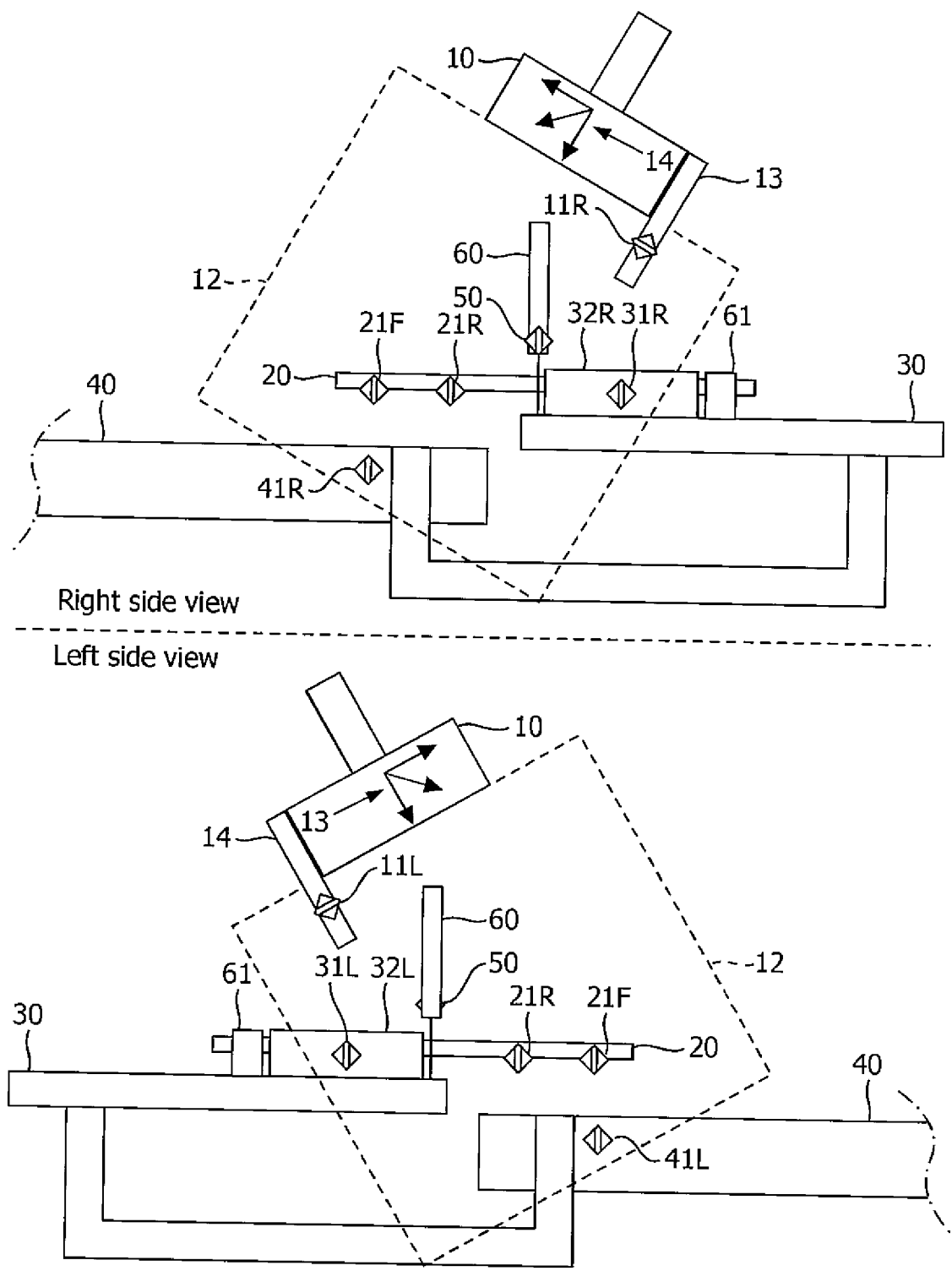
FIG. 2 illustrates an exemplary embodiment of a clinical set-up in accordance with the present invention.

Referring to FIGS. 1 and 2, those having ordinary skill in the art will appreciate additional embodiments for equipping EM generator 10, ultrasound probe 20, ultrasound stepper 30 and patient table 40 with QA electromagnetic sensor(s) including, but not limited to, QA electromagnetic sensor(s) being positioned in different configurations than shown in FIG. 2, and QA electromagnetic sensor trios.

Referring back to FIG. 1, the QA assessment of the present invention further incorporates, into the clinical set-up, a QA machine 70 employing a monitor 71, an interface platform 72, a workstation 73 and a QA controller 74 installed within workstation 73.

QA controller 74 includes and/or is accessible by an operating system (not shown) as known in the art for controlling various graphical user interfaces, data and images on monitor 71 as directed by a workstation operator (e.g., a doctor, technician, etc.) via a keyboard, buttons, dials, joysticks, etc. of interface platform 72, and for storing/reading data as programmed and/or directed by the workstation operator of interface platform 72.

Workstation 73 may be connected/coupled to the electromagnetic sensors as known in the art to input sensor data SD to be processed by QA controller 74 for EMF QA assessment purposes. To this end, workstation 73 includes an EM sensor monitoring module 75 for monitoring a sensed position of each quality assurance electromagnetic sensor within FOV 12 of the EMF, and a quality assessment module 76 assessing the tracking quality of the EMF derived from the sensed position monitoring by module 75.

Figure 3:
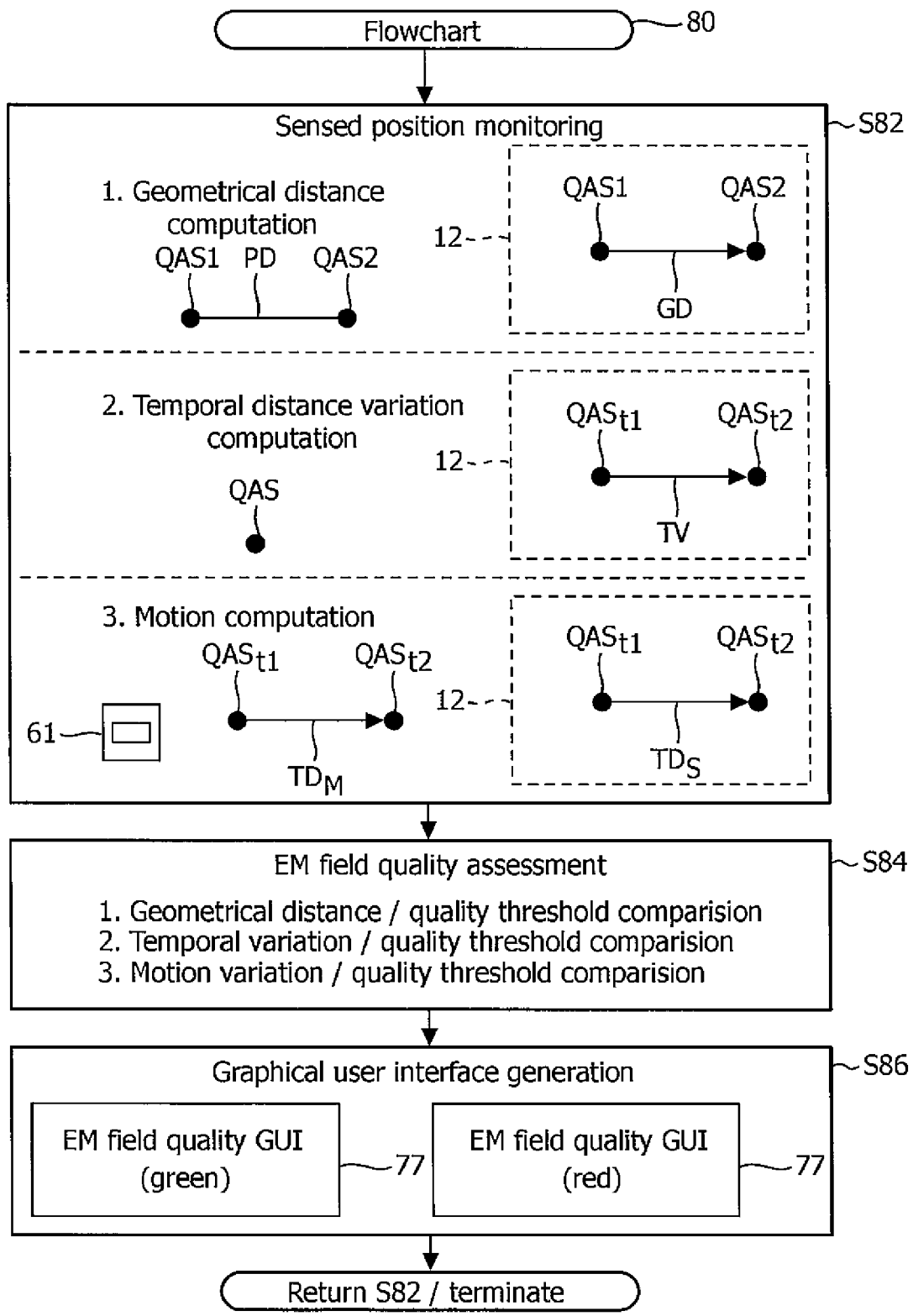
FIG. 3 illustrates an exemplary embodiment of a flowchart representative of an EMF quality assurance method of the present invention.

To facilitate an understanding of modules 75 and 76, FIG. 3 illustrates a flowchart 80 representative of an EMF QA method of the present invention.

Referring to FIG. 3, a stage S82 of flowchart 80 encompasses EM sensor monitoring module 75 (FIG. 1) executing one or more of four sensed position monitoring modes. In practice, the position monitoring by module 75 for all modes is executed relative to a coordinate system associated with an emission of the EMF including, but not limited, an internal coordinate system 14 of EMF generator 10 as shown in FIGS. 1 and 2 and a reference coordinate system of reference electromagnetic sensor 50 as known in the art.

Absolute Distance Mode (exemplarily shown in stage S82). For this mode, module 76 knows a physical distance PD between a pair of electromagnetic sensors QAS1 and QAS2 (e.g., sensor pair 11, sensor pair 21, sensor pair 31 or sensor pair 41 of FIG. 1). In exemplarily operation as shown, module 75 monitor a sensed position of each electromagnetic sensors QAS1 and QAS2 within FOV 12 of the EMF. Based on the sensed positions by module 75, module 76 computes a geometrical distance GD between electromagnetic sensors QAS1 and QAS2 for quality assessment purposes subsequently described herein during a stage S84 of flowchart 80. In practice, geometrical distance GD may be computed as a magnitude of a vector extending between electromagnetic sensors QAS1 and QAS2.

Temporal Positioning Mode (exemplarily shown in stage S82). For this mode, module 75 monitors a sensed position of a single electromagnetic sensor QAS at two or more discrete time instances 1 . . . N corresponding to electromagnetic sensor QAS being stationary within FOV 12 of the EMF. For example, QA electromagnetic sensors 11R/11L, 21R/21L, 31R/31L and 50 of FIG. 2 being stationary within FOV 12 of the EMF.

In exemplarily operation as shown, module 75 monitors a sensed position of QA electromagnetic sensor QAS within FOV 12 of the EMF at a time t1 and a time t2. Based on the temporal position sensing, module 76 computes a temporal position variation TPV of electromagnetic sensor QAS for quality assessment purposes subsequently described herein during stage S84 of flowchart 80. In practice, temporal position variation TPV may be computed as a magnitude of a vector, if any, extending between the sensed temporal positions of electromagnetic sensor QAS.

Encoded Translation Mode (exemplarily shown in stage S82). For this mode, at two or more discrete time instances 1 . . . N, module 75 monitors a sensed translational movement of electromagnetic sensor QAS of ultrasound probe 20 (FIG. 2) controlled by ultrasound stepper 30 (FIG. 2), while encoder 61 (FIG. 2) concurrently measures the translational movement of electromagnetic sensor QAS of ultrasound probe 20 controlled by ultrasound stepper 30.

More particularly for example, in operation as ultrasound probe 20 is being translated by ultrasound stepper 30, encoder 61 measures a translation distance $TD_M$ of electromagnetic sensor QAS at a beginning time t1 and an ending time t2. Concurrently, module 75 monitors a sensed positioning of electromagnetic sensor QAS within FOV 12 of the EMF at beginning time t1 and ending time t2. Based on the sensed positioning, module 76 computes a sensed translation distance $TD_S$ of electromagnetic sensor QAS within FOV 12 of the EMF and further computes of absolute motion variation between translation distance $TD_M$ and sensed translation distance $TD_S$ for quality assessment purposes subsequently described herein during stage S84 of flowchart 80. In practice, sensed translation distance $TD_S$ may be computed as a magnitude of a vector, if any, extending between the sensed translation positions of electromagnetic sensor QAS.

Encoded Rotation Mode (not exemplarily shown in stage S82). For this mode, at two or more discrete time instances 1 . . . N, module 75 monitors a sensed rotational movement of electromagnetic sensor QAS of ultrasound probe 20 controlled by ultrasound stepper 30, while encoder 61 concurrently measures the rotational movement of electromagnetic sensor QAS of ultrasound probe 20 controlled by ultrasound stepper 30.

More particularly for example, in operation as ultrasound probe 20 is being rotated by ultrasound stepper 30, encoder 61 measures a rotational distance of electromagnetic sensor QAS at a beginning time t1 and an ending time t2. Concurrently, module 75 monitors a sensed positioning of electromagnetic sensor QAS within FOV 12 of the EMF at beginning time t1 and ending time t2. Based on the sensed positioning, module 76 computes a sensed rotational distance of electromagnetic sensor QAS within FOV 12 of the EMF and further computes an absolute motion variation between the measured rotational distance and the sensed rotational distance for quality assessment purposes subsequently described herein during stage S84 of flowchart 80. In practice, the sensed rotational distance may be computed as a magnitude of a vector, if any, extending between the sensed rotation positions of electromagnetic sensor QAS.

Still referring to FIG. 3, a stage S84 of flowchart 80 encompasses quality assessment module 76 (FIG. 1) assessing a quality of EMF field 12 (FIG. 1) and a stage S85 of flowchart 80 generating a graphical user interface ("GUI") 77 illustrative of the assessed quality of EMF field 12. The following table highlights various assessments and GUI for the previously described monitoring modes.

| MODE | COMPARISON | ASSESSMENT | GUI |
|---|---|---|---|
| SENSOR PAIR | $\|GD-PD\| \leq QT$ | RELIABLE | GREEN |
| SENSOR PAIR | $\|GD-PD\| > QT$ | UNRELIABLE | RED |
| SINGLE SENSOR | $TPV \leq QT$ | RELIABLE | GREEN |
| SINGLE SENSOR | $TPV > QT$ | UNRELIABLE | RED |
| TRANSLATION | $\|TD_M\text{-}TD_S\| \leq QT$ | RELIABLE | GREEN |
| TRANSLATION | $\|TD_M\text{-}TD_S\| > QT$ | UNRELIABLE | RED |
| ROTATION | $\|RD_M\text{-}RD_S\| \leq QT$ | RELIABLE | GREEN |
| ROTATION | $\|RD_M\text{-}RD_S\| > QT$ | UNRELIABLE | RED |

Absolute Distance Mode. Module 76 computes an absolute error differential between computed geometrical distance GD and known physical distance PD. Module 76 deems EMF field 12 as being reliable for tracking purposes if the error differential is less than or equal to a quality threshold QT. Otherwise, module 76 deems EMF field 12 as being unreliable for tracking purposes.

Temporal Positioning Mode. Module 76 deems EMF field 12 as being reliable for tracking purposes if temporal position variation TPV is less than or equal to quality threshold QT. Otherwise, module 76 deems EMF field 12 as being unreliable for tracking purposes. Encoded Translation Mode, Module 76 deems EMF field 12 as being reliable for tracking purposes if an absolute motion variation between measured translation distance $TD_M$ and sensed translation distance $TD_S$ is less than or equal to quality threshold QT. Otherwise, module 76 deems EMF field 12 as being unreliable for tracking purposes.

Encoded Rotational Mode, Module 76 deems EMF field 12 as being reliable for tracking purposes if an absolute motion variation between measured rotation distance $RD_M$ and sensed rotation distance $RD_S$ is less than or equal to quality threshold QT. Otherwise, module 76 deems EMF field 12 as being unreliable for tracking purposes.

In practice, a numerical value for quality threshold QT is derived from testing and training set of sensed data and is therefore dependent upon a particular clinical set-up arrangement.

Modules 75 and 76 will sequentially repeat stages S82-S86 as needed during a calibration, quality assurance and/or EM guidance of the clinical set-up. More particular to EM guidance, referring back to FIG. 1, GUI 77 will be displayed in conjunction with an ultrasound ("US") image 78 generated by ultrasound probe 20 whereby the reliability of tracking an interventional tool within ultrasound image 78 is communicated in real-time to an operator.

Referring to FIGS. 1-3, from the description of the exemplary embodiments of a mounting arm and intervention workstation of the present invention, those having ordinary skill in the art will appreciate numerous benefits of the present invention including, but not limited to, a facilitation of a reliable positioning of a EMF generator in any EM-guided interventional procedure.

Furthermore, as one having ordinary skill in the art will appreciate in view of the teachings provided herein, features, elements, components, etc. described in the present disclosure/specification and/or depicted in the FIGS. 1-3 may be implemented in various combinations of electronic components/circuitry, hardware, executable software and executable firmware, particularly as application modules of a quality assurance controller as described herein, and provide functions which may be combined in a single element or multiple elements. For example, the functions of the various features, elements, components, etc. shown/illustrated/depicted in the FIGS. 1-3 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown. Furthermore, exemplary embodiments of the present invention can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk read only memory (CD-ROM), compact disk read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments of novel and inventive system and method for tracking quality control of electromagnetic guidance, (which embodiments are intended to be illustrative and not limiting), it is noted that modifications and variations can be made by persons having ordinary skill in the art in light of the teachings provided herein, including the FIGS. 1-3. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

The invention claimed is:

1. An electromagnetic field quality assurance system, comprising:
    an electromagnetic field generator operable to emit an electromagnetic field;
    at least one quality assurance electromagnetic sensor operable to sense an emission of the electromagnetic field by the electromagnetic field generator; and
    a quality assurance controller operable in communication with the at least one quality assurance electromagnetic sensor, wherein the quality assurance controller is configured to:
        monitor a sensed position of the at least one quality assurance electromagnetic sensor within a field-of-view of the electromagnetic field during an interventional procedure,
        compare the sensed position of the at least one quality assurance electromagnetic sensor with an independently determined position of the at least one quality assurance electromagnetic sensor during the interventional procedure, and in response to the comparison to produce a variation between the sensed position and the independently determined position,
        assess a tracking quality of the electromagnetic field during the interventional procedure based on a comparison between the variation and a non-zero quality threshold, and
        provide to a user during the interventional procedure, via a user interface, a real-time indication of whether the assessed tracking quality of the electromagnetic field is determined to be reliable for tracking purposes, or whether the tracking quality of the electromagnetic field is determined to be unreliable for tracking purposes.

2. The electromagnetic field quality assurance system of claim 1, further comprising:
    an ultrasound stepper,
    wherein the ultrasound stepper is configured to translationally move the at least one quality assurance electromagnetic sensor within the field-of-view of the electromagnetic field,
    wherein the ultrasound stepper includes an encoder which is configured to measure a translational distance that the ultrasound stepper moves the at least one quality assurance electromagnetic sensor within the field-of-view of the electromagnetic field during a time interval,
    wherein the quality assurance controller is configured to monitor a sensed translational distance which an ultrasound stepper moves the at least one quality assurance electromagnetic sensor within the field-of-view of the electromagnetic field during a time interval, based on the sensed position of the at least one quality assurance electromagnetic sensor, and
    wherein the quality assurance controller is configured to produce an absolute translational motion variation as a difference between: the measured translational distance during the time interval, measured by the encoder, and the sensed translational distance for the at least one quality assurance electromagnetic sensor within the field-of-view of the electromagnetic field during the time interval, monitored by the quality assurance controller,
    wherein the quality assurance controller is further configured to determine that the electromagnetic field is not reliable for tracking purposes when the absolute translational motion variation is not greater than the non-zero quality threshold, and
    wherein the quality assurance controller is further configured to determine that the electromagnetic field is reliable for tracking purposes when the absolute translational motion variation is greater than the non-zero quality threshold.

3. The electromagnetic field quality assurance system of claim 1,
    wherein the quality assurance controller is operable to compute a geometrical distance between a pair of quality assurance electromagnetic sensors as a function of sensed positions of the pair of quality assurance electromagnetic sensors within the field-of-view of the electromagnetic field.

4. The electromagnetic field quality assurance system of claim 3, wherein the quality assurance controller is operable to compute the variation as an absolute error differential between the computed geometrical distance, and a known physical distance between the pair of quality assurance electromagnetic sensors.

5. The electromagnetic field quality assurance system of claim 1,
    wherein the at least one quality assurance electromagnetic sensor within the field-of-view of the electromagnetic field includes a first quality assurance electromagnetic sensor within the field-of-view of the electromagnetic field, and
    wherein the quality assurance controller is operable to compute a temporal position variation of a sensed position of the first quality assurance electromagnetic sensor within the field-of-view of the electromagnetic field.

6. The electromagnetic field quality assurance system of claim 5, wherein the quality assurance controller is operable to compare the temporal position variation to the non-zero quality threshold.

7. The electromagnetic field quality assurance system of claim 1, wherein the at least one quality assurance electromagnetic sensor within the field-of-view of the electromagnetic field includes a first quality assurance electromagnetic sensor within the field-of-view of the electromagnetic field, the system further comprising an ultrasound probe equipped with the first quality assurance electromagnetic sensor,
    wherein the quality assurance controller is operable in electrical communication with the first quality assurance sensor to sense a motion of the first quality assurance electromagnetic sensor within the field-of-view of the electromagnetic field, and wherein the quality assurance controller is further operable to compute a motion variation between a sensed motion of the first quality assurance electromagnetic sensor within the field-of-view of the electromagnetic field and a measured motion of the ultrasound probe by the encoder.

8. The electromagnetic field quality assurance system of claim 7, wherein the quality assurance controller is operable to compare the computed motion variation to the non-zero quality threshold.

9. A quality assurance controller for assessing a tracking quality of an emission of electromagnetic field by an electromagnetic field generator and sensed by at least one quality assurance electromagnetic sensor, the quality assurance controller comprising:

an electromagnetic sensor monitoring module operable to monitor a sensed position of the at least one quality assurance electromagnetic sensor within a field-of-view of the electromagnetic field during an interventional procedure;

a quality assessment module operable to:
compare the sensed position of the at least one quality assurance electromagnetic sensor with an independently determined position of the at least one quality assurance electromagnetic sensor during the interventional procedure,
produce, in response to the comparison, a variation between the sensed position and the independently determined position,
assess the tracking quality of the electromagnetic field during the interventional procedure based on a comparison between the variation and a non-zero quality threshold, and
provide a signal to a user interface to provide to a user, during the interventional procedure, a real-time indication of whether the assessed tracking quality of the electromagnetic field is determined to be reliable for tracking purposes, or whether the tracking quality of the electromagnetic field is determined to be unreliable for tracking purposes.

10. The quality assurance controller of claim 9,
wherein the electromagnetic sensor monitoring module is configured to monitor a sensed translational distance which an ultrasound stepper moves the at least one quality assurance electromagnetic sensor within the field-of-view of the electromagnetic field during a time interval based on the sensed position of the at least one quality assurance electromagnetic sensor;
wherein the quality assessment module is configured to receive from an encoder a measured translational distance which the ultrasound stepper moves the at least one quality assurance electromagnetic sensor within the field-of-view of the electromagnetic field during the time interval, measured by the encoder;
wherein the quality assurance controller is configured to produce an absolute translational motion variation as a difference between: the measured translational distance during the time interval, measured by the encoder, and the sensed translational distance for the at least one quality assurance electromagnetic sensor within the field-of-view of the electromagnetic field during the time interval, monitored by the quality assurance controller;

wherein the quality assurance controller is configured to determine that the electromagnetic field is reliable for tracking purposes when the absolute translational motion variation is not greater than the non-zero quality threshold, and
wherein the quality assurance controller is configured to determine that the electromagnetic field is not reliable for tracking purposes when the absolute translational motion variation is greater than the non-zero quality threshold.

11. The quality assurance controller of claim 9,
wherein the electromagnetic sensor monitoring module is configured to monitor a sensed rotational distance which an ultrasound stepper moves the at least one quality assurance electromagnetic sensor within the field-of-view of the electromagnetic field during a time interval based on the sensed position of the at least one quality assurance electromagnetic sensor;
wherein the quality assessment module is configured to receive from an encoder a measured rotational distance which the ultrasound stepper moves the at least one quality assurance electromagnetic sensor within the field-of-view of the electromagnetic field during the time interval, measured by the encoder;
wherein the quality assurance controller is configured to produce an absolute rotational motion variation as a difference between: the measured rotational distance during the time interval, measured by the encoder, and the sensed rotational distance for the at least one quality assurance electromagnetic sensor within the field-of-view of the electromagnetic field during the time interval, monitored by the quality assurance controller,
wherein the quality assurance controller is configured to determine that the electromagnetic field is reliable for tracking purposes when the absolute rotational motion variation is not greater than the non-zero quality threshold, and
wherein the quality assurance controller is configured to determine that the electromagnetic field is not reliable for tracking purposes when the absolute rotational motion variation is greater than the non-zero quality threshold.

12. A method, comprising:
an electromagnetic field generator emitting an electromagnetic field;
at least one quality assurance electromagnetic sensor sensing an emission of the electromagnetic field by the electromagnetic field generator;
a quality assurance controller:
monitoring a sensed position of the at least one quality assurance electromagnetic sensor within a field-of-view of the electromagnetic field during an interventional procedure,
comparing the sensed position of the at least one quality assurance electromagnetic sensor with an independently determined position of the at least one quality assurance electromagnetic sensor during the interventional procedure,
producing, in response to the comparison, a variation between the sensed position and the independently determined position,
assessing a tracking quality of the electromagnetic field during the interventional procedure based on a comparison between the variation and a non-zero quality threshold, and
providing a signal to a user interface to provide to a user, during the interventional procedure, a real-time indication of whether the assessed tracking quality of the electromagnetic field is determined to be reliable for tracking purposes, or whether the tracking quality of the electromagnetic field is determined to be unreliable for tracking purposes.

13. The method of claim 12, comprising:
an ultrasound stepper translationally moving the at least one quality assurance electromagnetic sensor within the field-of-view of the electromagnetic field;
an encoder measuring a translational distance that the ultrasound stepper moves the at least one quality assurance electromagnetic sensor within the field-of-view of the electromagnetic field during a time interval;
the quality assurance controller monitoring a sensed translational distance which an ultrasound stepper moves the at least one quality assurance electromagnetic sensor within the field-of-view of the electromagnetic field during a time interval based on the sensed position of the at least one quality assurance electromagnetic sensor;
the quality assurance controller producing an absolute translational motion variation as a difference between: the measured translational distance during the time interval, measured by the encoder, and the sensed translational distance for the at least one quality assurance electromagnetic sensor within the field-of-view of the electromagnetic field during the time interval, monitored by the quality assurance controller;
the quality assurance controller determining that the electromagnetic field is reliable for tracking purposes when the absolute translational motion variation is not greater than the non-zero quality threshold, and
the quality assurance controller determining that the electromagnetic field is not reliable for tracking purposes when the absolute translational motion variation is greater than the non-zero quality threshold.

14. The method of claim 12, comprising:
an ultrasound stepper rotationally moving the at least one quality assurance electromagnetic sensor within the field-of-view of the electromagnetic field;
an encoder measuring a rotational distance that the ultrasound stepper moves the at least one quality assurance electromagnetic sensor within the field-of-view of the electromagnetic field during a time interval;
the quality assurance controller producing an absolute rotational motion variation as a difference between: the measured rotational distance during the time interval, measured by the encoder, and a monitored rotational distance for the at least one quality assurance electromagnetic sensor within the field-of-view of the electromagnetic field during the time interval, monitored by the quality assurance controller;
the quality assurance controller determining that the electromagnetic field is reliable for tracking purposes when the absolute rotational motion variation is not greater than the non-zero quality threshold, and
the quality assurance controller determining that the electromagnetic field is not reliable for tracking purposes when the absolute rotational motion variation is greater than the non-zero quality threshold.

15. The method of claim 12, wherein the at least one quality assurance electromagnetic sensor within the field-of-view of the electromagnetic field includes a first quality assurance electromagnetic sensor within the field-of-view of the electromagnetic field, and wherein the method comprises:

the quality assurance controller monitoring the sensed position of the first quality assurance electromagnetic sensor within the field-of-view of the electromagnetic field at a first time;
the quality assurance controller monitoring the sensed position of the first quality assurance electromagnetic sensor within the field-of-view of the electromagnetic field at a second time subsequent to the first time, wherein the first quality assurance electromagnetic sensor is stationary within the field-of-view of the electromagnetic field from the first time to the second time;
the quality assurance controller producing a temporal position variation as a difference between: the sensed position of the first quality assurance electromagnetic sensor within the field-of-view of the electromagnetic field at the second time, and the sensed position of the first quality assurance electromagnetic sensor within the field-of-view of the electromagnetic field at the first time;
the quality assurance controller determining that the electromagnetic field is reliable for tracking purposes when the temporal position variation is not greater than the non-zero quality threshold, and
the quality assurance controller determining that the electromagnetic field is not reliable for tracking purposes when the temporal position variation is greater than the non-zero quality threshold.

16. The method of claim 12, wherein the at least one quality assurance electromagnetic sensor within the field-of-view of the electromagnetic field includes a first quality assurance electromagnetic sensor within the field-of-view of the electromagnetic field, and includes a second quality assurance electromagnetic sensor within the field-of-view of the electromagnetic field, wherein there is an actual physical distance between the first quality assurance electromagnetic sensor and the second quality assurance electromagnetic sensor, wherein the method comprises:
the quality assurance controller monitoring the sensed position of the first quality assurance electromagnetic sensor within the field-of-view of the electromagnetic field;
the quality assurance controller monitoring the sensed position of the second quality assurance electromagnetic sensor within the field-of-view of the electromagnetic field;
the quality assurance controller determining a sensed geometric distance between the first quality assurance electromagnetic sensor and the second quality assurance electromagnetic sensor based on the sensed position of the first quality assurance electromagnetic sensor and the sensed position of the second quality assurance electromagnetic sensor;
the quality assurance controller producing an absolute error differential as a difference between: the sensed geometric distance between the first quality assurance electromagnetic sensor and the second quality assurance electromagnetic sensor, and the actual physical distance between the first quality assurance electromagnetic sensor and the second quality assurance electromagnetic sensor;
the quality assurance controller determining that the electromagnetic field is reliable for tracking purposes when the absolute error differential is not greater than the non-zero quality threshold, and the quality assurance controller determining that the electromagnetic field is not reliable for tracking purposes when the absolute error differential is greater than the non-zero quality threshold.

\* \* \* \* \*